(12) United States Patent
Gunday et al.

(10) Patent No.: US 9,468,365 B2
(45) Date of Patent: Oct. 18, 2016

(54) COMPACT LIGHT SOURCE

(71) Applicants: Erhan H. Gunday, Great Neck, NY (US); Lawrence J. Gerrans, San Anselmo, CA (US); Alex Hsia, San Jose, CA (US)

(72) Inventors: Erhan H. Gunday, Great Neck, NY (US); Lawrence J. Gerrans, San Anselmo, CA (US); Alex Hsia, San Jose, CA (US)

(73) Assignee: Sanovas, Inc., Sausalito, CA (US)

( * ) Notice: Subject to any disclaimer, the term of this patent is extended or adjusted under 35 U.S.C. 154(b) by 210 days.

(21) Appl. No.: 13/837,664

(22) Filed: Mar. 15, 2013

(65) Prior Publication Data

US 2014/0275806 A1    Sep. 18, 2014

(51) Int. Cl.
*A61B 1/06* (2006.01)
*A61B 1/00* (2006.01)
*A61B 1/04* (2006.01)
(Continued)

(52) U.S. Cl.
CPC .............. *A61B 1/06* (2013.01); *A61B 1/00154* (2013.01); *A61B 1/04* (2013.01); *A61B 1/0669* (2013.01); *A61B 1/0684* (2013.01); *A61B 1/07* (2013.01); *A61B 1/128* (2013.01); *A61B 17/320725* (2013.01); *A61B 90/30* (2016.02); *A61B 17/24* (2013.01); *A61B 2017/22061* (2013.01);
(Continued)

(58) Field of Classification Search
CPC .... A61B 1/06; A61B 1/0607; A61B 1/0615; A61B 1/0623; A61B 1/063; A61B 1/0638; A61B 1/0646; A61B 1/0653; A61B 1/0661; A61B 1/0669; A61B 1/0676; A61B 1/0684; A61B 1/0692; A61B 1/07; A61B 17/02; A61B 17/0206; A61B 17/0218; A61B 17/0231; A61B 2017/0212; A61B 2017/0225; A61B 2017/0237; A61B 2017/0243; A61B 19/52; A61B 19/5202; A61B 19/5204; A61B 19/5206; A61B 19/5208; A61B 2019/521; A61B 2019/5204; A61B 2019/5206; A61B 2019/5208
USPC ............................................................ 362/294
See application file for complete search history.

(56) References Cited

U.S. PATENT DOCUMENTS 4,981,470 A    1/1991    Bombeck, IV
5,007,898 A    4/1991    Rosenbluth et al.
(Continued)

FOREIGN PATENT DOCUMENTS

WO    2012091364 A2    7/2012

OTHER PUBLICATIONS

International Search Report and Written Opinion of the International Searching Authority Application No. PCT/US2014/018948 Completed: Nov. 14, 2014; Mailing Date: Dec. 8, 2014 7 pages.
(Continued)

*Primary Examiner* — Christian Sevilla
*Assistant Examiner* — Eric S Gibson
(74) *Attorney, Agent, or Firm* — St Onge Steward Johnson and Reens LLC

(57) ABSTRACT

A compact light source includes an LED for supplying light and an optical element that receives and transmits the light. The LED is disposed in an insulation housing to insulate the LED, which has a surface that conducts the heat it generates. A heat sink is coupled to the LED adjacent the conductive surface, and a thermal compound is sandwiched in between the heat sink and conductive surface in order to channel and dissipate the heat generated by the LED without heating up any surrounding structures. In some embodiments, the optical element is part of a collimator coupled to the insulation housing and is a doublet or plano convex lens.

22 Claims, 5 Drawing Sheets

(51) Int. Cl.
  *A61B 17/3207* (2006.01)
  *A61B 1/07* (2006.01)
  *A61B 1/12* (2006.01)
  *A61M 25/10* (2013.01)
  *A61B 17/24* (2006.01)
  *A61B 17/22* (2006.01)

(52) U.S. Cl.
  CPC .... *A61B2090/306* (2016.02); *A61B 2090/309* (2016.02); *A61M 25/10181* (2013.11)

(56) References Cited

U.S. PATENT DOCUMENTS

| | | | |
|---|---|---|---|
| 5,090,959 A | 2/1992 | Samson et al. | |
| 5,316,016 A | 5/1994 | Adams et al. | |
| 5,537,304 A * | 7/1996 | Klaus | 362/373 |
| 5,749,848 A | 5/1998 | Jang et al. | |
| 5,967,984 A | 10/1999 | Chu et al. | |
| 6,023,542 A | 2/2000 | Pan et al. | |
| 6,045,240 A * | 4/2000 | Hochstein | 362/294 |
| 6,084,354 A * | 7/2000 | Kohmura et al. | 315/57 |
| 6,102,929 A | 8/2000 | Conway et al. | |
| 6,787,999 B2 * | 9/2004 | Stimac et al. | 315/51 |
| 7,198,397 B2 * | 4/2007 | Bennett et al. | 362/574 |
| 7,264,624 B2 | 9/2007 | Nash et al. | |
| 7,668,450 B2 * | 2/2010 | Todd et al. | 396/117 |
| 7,736,336 B2 | 6/2010 | Plishka et al. | |
| 7,871,184 B2 * | 1/2011 | Peng | 362/294 |
| 7,874,699 B2 * | 1/2011 | Liang | 362/249.02 |
| 7,914,517 B2 | 3/2011 | Baran et al. | |
| 7,988,633 B2 | 8/2011 | Hossack et al. | |
| 8,070,329 B1 | 12/2011 | Bechtel et al. | |
| 8,172,834 B2 | 5/2012 | Bhadri et al. | |
| 8,177,397 B1 * | 5/2012 | Knoble et al. | 362/373 |
| 8,206,015 B2 * | 6/2012 | Cho et al. | 362/311.02 |
| 8,206,374 B2 | 6/2012 | Duane et al. | |
| 8,226,601 B2 | 7/2012 | Gunday et al. | |
| 8,242,669 B2 * | 8/2012 | Qiu | 313/46 |
| 8,246,230 B2 * | 8/2012 | Todd et al. | 362/574 |
| 8,258,682 B2 * | 9/2012 | Villard | 313/46 |
| 8,272,762 B2 * | 9/2012 | Maxik et al. | 362/249.02 |
| 8,299,693 B2 * | 10/2012 | Chen | 313/46 |
| 8,419,225 B2 * | 4/2013 | Zeng et al. | 362/294 |
| 8,419,240 B2 * | 4/2013 | Lim | 362/373 |
| 8,427,059 B2 * | 4/2013 | Betsuda et al. | 315/32 |
| 8,430,533 B1 * | 4/2013 | Blalock et al. | 362/294 |
| 8,434,917 B2 * | 5/2013 | Lai | 362/373 |
| 8,449,169 B2 * | 5/2013 | Maslowski et al. | 362/646 |
| 8,474,999 B2 * | 7/2013 | Ou et al. | 362/249.02 |
| 8,492,961 B2 * | 7/2013 | Zeng | 313/46 |
| 8,500,316 B2 * | 8/2013 | Hisayasu et al. | 362/547 |
| 8,517,576 B2 * | 8/2013 | Yang et al. | 362/373 |
| 8,562,181 B2 * | 10/2013 | Dong et al. | 362/294 |
| 8,579,471 B2 * | 11/2013 | Boomgaarden et al. | 362/294 |
| 8,585,249 B2 * | 11/2013 | Huang | 362/294 |
| 8,591,069 B2 * | 11/2013 | Horn | 362/294 |
| 8,602,597 B2 * | 12/2013 | Lopez et al. | 362/294 |
| 8,608,341 B2 * | 12/2013 | Boomgaarden et al. | 362/249.02 |
| 8,646,942 B2 * | 2/2014 | Boomgaarden et al. | 362/249.02 |
| 8,651,705 B2 * | 2/2014 | Wilcox et al. | 362/294 |
| 8,680,755 B2 * | 3/2014 | Lim et al. | 313/46 |
| 8,684,563 B2 * | 4/2014 | Lin et al. | 362/294 |
| 8,686,623 B2 * | 4/2014 | Wheelock et al. | 313/36 |
| 8,686,641 B2 * | 4/2014 | Maxik et al. | 315/113 |
| 8,696,170 B2 * | 4/2014 | Huang | 362/294 |
| 2003/0214810 A1 * | 11/2003 | Zhang | 362/294 |
| 2004/0230116 A1 | 11/2004 | Cowan et al. | |
| 2005/0007783 A1 * | 1/2005 | Ono | 362/294 |
| 2005/0041428 A1 * | 2/2005 | Zhang | 362/294 |
| 2005/0158687 A1 * | 7/2005 | Dahm | 433/29 |
| 2006/0061997 A1 * | 3/2006 | Lin | 362/294 |
| 2006/0274529 A1 * | 12/2006 | Cao | 362/294 |
| 2006/0282153 A1 | 12/2006 | Jang | |
| 2007/0133209 A1 * | 6/2007 | Wang et al. | 362/294 |
| 2007/0211470 A1 * | 9/2007 | Huang | 362/294 |
| 2007/0230186 A1 * | 10/2007 | Chien | 362/294 |
| 2007/0236935 A1 * | 10/2007 | Wang | 362/294 |
| 2007/0253202 A1 * | 11/2007 | Wu et al. | 362/294 |
| 2007/0285926 A1 * | 12/2007 | Maxik | 362/294 |
| 2008/0212325 A1 * | 9/2008 | Wang | 362/294 |
| 2008/0253125 A1 * | 10/2008 | Kang et al. | 362/294 |
| 2008/0266866 A1 * | 10/2008 | Tsai | 362/294 |
| 2008/0291401 A1 * | 11/2008 | Lo et al. | 353/58 |
| 2009/0002995 A1 * | 1/2009 | Lee et al. | 362/294 |
| 2009/0009999 A1 * | 1/2009 | Wang et al. | 362/249 |
| 2009/0021944 A1 * | 1/2009 | Lee et al. | 362/294 |
| 2009/0034261 A1 * | 2/2009 | Grove | 362/294 |
| 2009/0046464 A1 * | 2/2009 | Liu et al. | 362/294 |
| 2009/0046465 A1 * | 2/2009 | Hashimoto et al. | 362/294 |
| 2009/0059595 A1 * | 3/2009 | Ge | 362/294 |
| 2009/0103294 A1 * | 4/2009 | Zhang et al. | 362/234 |
| 2009/0103296 A1 * | 4/2009 | Harbers et al. | 362/234 |
| 2009/0141500 A1 * | 6/2009 | Peng | 362/294 |
| 2009/0147520 A1 * | 6/2009 | Liu et al. | 362/294 |
| 2009/0153797 A1 * | 6/2009 | Allon et al. | 351/206 |
| 2009/0154166 A1 * | 6/2009 | Zhang et al. | 362/294 |
| 2009/0175041 A1 * | 7/2009 | Yuen et al. | 362/294 |
| 2009/0192494 A1 | 7/2009 | Michishita et al. | |
| 2009/0264866 A1 | 10/2009 | Powell | |
| 2009/0284155 A1 * | 11/2009 | Reed et al. | 315/32 |
| 2009/0290382 A1 * | 11/2009 | Liao | 362/645 |
| 2009/0296402 A1 * | 12/2009 | Chang et al. | 362/294 |
| 2010/0110691 A1 * | 5/2010 | Hsu et al. | 362/294 |
| 2010/0121270 A1 | 5/2010 | Gunday et al. | |
| 2010/0149818 A1 * | 6/2010 | Ruffin | 362/294 |
| 2010/0195329 A1 * | 8/2010 | Inoue et al. | 362/235 |
| 2010/0232164 A1 * | 9/2010 | Tessnow et al. | 362/294 |
| 2010/0296272 A1 * | 11/2010 | Roos et al. | 362/147 |
| 2011/0044039 A1 * | 2/2011 | Chung et al. | 362/235 |
| 2011/0044049 A1 * | 2/2011 | Boyer | 362/287 |
| 2011/0044050 A1 * | 2/2011 | Chiu | 362/294 |
| 2011/0057552 A1 * | 3/2011 | Weaver | 313/46 |
| 2011/0128730 A1 * | 6/2011 | Chiu | 362/235 |
| 2011/0152683 A1 | 6/2011 | Gerrans et al. | |
| 2011/0164420 A1 * | 7/2011 | Lee | 362/249.02 |
| 2011/0222291 A1 * | 9/2011 | Peng | 362/294 |
| 2011/0260647 A1 * | 10/2011 | Catalano et al. | 315/294 |
| 2012/0057352 A1 * | 3/2012 | Wilcox | F21K 9/54 362/308 |
| 2012/0081904 A1 * | 4/2012 | Horng | 362/294 |
| 2012/0120635 A1 * | 5/2012 | Strong et al. | 362/105 |
| 2012/0140462 A1 * | 6/2012 | Pickard | 362/231 |
| 2012/0140465 A1 * | 6/2012 | Rowlette et al. | 362/235 |
| 2012/0155059 A1 * | 6/2012 | Hoelen et al. | 362/84 |
| 2012/0162994 A1 * | 6/2012 | Wasniewski et al. | 362/294 |
| 2012/0238816 A1 | 9/2012 | Gunday et al. | |
| 2012/0241781 A1 * | 9/2012 | Yuan et al. | 257/89 |
| 2012/0259217 A1 | 10/2012 | Gerrans et al. | |
| 2012/0291259 A1 | 11/2012 | Popovich et al. | |
| 2013/0100674 A1 * | 4/2013 | Kim et al. | 362/249.14 |
| 2013/0223061 A1 * | 8/2013 | Hwu et al. | 362/235 |
| 2013/0258672 A1 * | 10/2013 | Bell | 362/294 |
| 2013/0294085 A1 * | 11/2013 | Watanabe et al. | 362/294 |
| 2013/0301275 A1 * | 11/2013 | Kim | 362/294 |
| 2014/0275806 A1 * | 9/2014 | Gunday | A61B 1/0669 600/249 |

OTHER PUBLICATIONS

International Search Report and Written Opinion of the International Searching Authority Application No. PCT/2014/024302 Completed: Aug. 29, 2014; Mailing Date: Sep. 16, 2014 11 pages.
International Search Report and Written Opinion of the International Searching Authority Application No. PCT/US2014/017539 Completed: May 19, 2014; Mailing Date: Jun. 13, 2014 9 pages.

* cited by examiner

COMPACT LIGHT SOURCE

FIELD OF THE INVENTION

The present invention relates to an apparatus for providing light in medical environments. More specifically, the invention relates to a light source where the emitted heat from a bright light source is controlled.

BACKGROUND OF THE INVENTION

Non-invasive medical techniques have greatly increased the ease and success with which diagnostic and surgical procedures can be performed. As just one example, the treatment of pulmonary cancer has been advanced by the development of resector balloon catheters, such as that disclosed in U.S. Pat. No. 8,226,601 to Gunday et al., the specification of which is hereby incorporated by reference herein in its entirety.

In order to perform such non-invasive procedures, devices must be employed that allow the internal anatomy of the patient to be viewed by the medical practitioner. Accordingly, various types of imaging devices, employing a wide variety of optical assemblies, have been used for this purpose. However, because the interior of the human body is almost completely dark, proper illumination of the target site inside the body is required in order to obtain useful images. Specifically, light must be delivered to the interior body, into the field of view of the imaging device, such that the reflected light can be captured and transmitted to an appropriate device for rendering those images.

In traditional operating environments, light is transmitted from an external light source into the patient. Since these light sources must be very bright in order to provide sufficient illumination for imaging, they tend to generate significant heat. Since they generate so much heat, which could damage any biological tissue with which they come into contact, it is common to use self-contained, external light sources. A typical example of this is described in U.S. Pat. Nos. 7,668,450 and 8,246,230 to Todd et al. As described therein, a typical light source unit includes a light bulb, a ballast power supply, controls, and cooling fans. These light source units are typically mounted on a rack or boom arm along with other self-contained units, such as camera control units, insufflators, and electrosurgical units. The light generated by this light source in supplied through a light guide, such as a fiber optic cable, which transmits the light to the instrument being used in the patient.

These light sources, which require a lot of space and power, have a number of disadvantages. First, they are inefficient, as they must generate extremely intense light in order to compensate for the distance the light must travel along the cable from the unit to the instrument. Additionally, they can create dangerous conditions by transmitting heat energy to the patient. Further, the light cable is both cumbersome and further adds to the hazard of having too many cables in an already crowded room that can trip the medical professional or supporting personnel.

Accordingly, it has been proposed to instead use LEDs as a source of illumination. Because they are so small, they can be integrated into the imaging device, much closer to the target site, and their high light output, low cost, longevity, and reliability make them a desirable solution.

However, LED based light sources can get very hot during operation, and thus, can cause burns and equipment damage due to these high operating temperatures. These problems are very prominent when the light source is integrated in a portable or handheld medical device, which the LED will heat up. This can be hazardous for the patient, who will be in direct contact with the hot imaging device or instrument housing the LED, or possibly the hot LED itself, which can result in burns. Likewise, the medical practitioner holding the medical device can likewise be burned, resulting in injury to the practitioner, as well as serious injury to the patient if the practitioner unexpectedly moves or drops the instrument as a result. Additionally, heat can damage the device housing the LED, such as the optical elements of the imaging device.

What is desired, therefore, is a light source that is sufficiently bright to illuminate the interior of a patient. What is further desired is a light source that can be incorporated into the medical imaging device being used on the patient. What is also desired is a light source that will not result in burns to the patient or medical practitioner.

SUMMARY OF THE INVENTION

Accordingly, it is an object of the present invention to provide a light source that has a light output sufficient to illuminate the interior of a patient.

It is also an object of the present invention to provide a light source that is sufficiently small to be incorporated into a handheld medical device.

It is a further object of the present invention to provide a light source that controls the heat that it generates in order to prevent injury to patients and medical professionals and prevent damage to the medical device.

In order to overcome the deficiencies of the prior art and to achieve at least some of the objects and advantages listed, the invention comprises a light source, including an LED for supplying light, the LED having a surface that conducts heat generated by the LED, an optical element that receives and transmits the light supplied by the LED, an insulation housing in which the LED is disposed for insulating the LED, a heat sink coupled to the insulation housing and having a surface adjacent to the surface of the LED that conducts heat, and a thermal compound disposed between the surface of the heat sink and the surface of the LED that conducts heat.

In certain advantageous embodiments, the insulation housing comprises polyimide.

In some embodiments, the invention further includes a collimator coupled to the insulation housing, wherein the optical element is disposed in the collimator. In certain embodiments, the collimator comprises a receptacle adapted to receive a fiber optic cable, and in some cases, the invention further includes a light guide coupled to the collimator.

In certain embodiments, the optical element comprises a positive lens. In some cases, the optical element comprises an aspheric lens. In some embodiments, the optical element comprises a plano-convex lens, and in others, the optical element comprises a doublet.

In certain embodiments, the invention further includes a filter for filtering the light supplied by the LED, which in some cases, comprises an infrared filter.

In some embodiments, the LED includes a condenser lens for transmitting the light. In certain embodiments, the heat sink comprises an aluminum fin heat sink.

In certain advantageous embodiments, the thermal compound comprises a silicone medium. In some cases, the thermal compound is ceramic based, in some cases, the thermal compound is metal based, and in other cases, the thermal compound is carbon based.

In some embodiments, the surface of the LED that conducts heat comprises metal. In certain embodiments, the LED is pulse-width modulated to control its light output. In some cases, the insulation housing and the heat sink are threaded such that the housing and heat sink screw together.

In certain advantageous embodiments, the invention further comprised an imaging module having a wall with a hole passing therethrough, wherein the insulation housing is at least partially disposed in the hole and mounted to the wall of the imaging module.

DETAILED DESCRIPTION OF THE INVENTION

Figure 1:
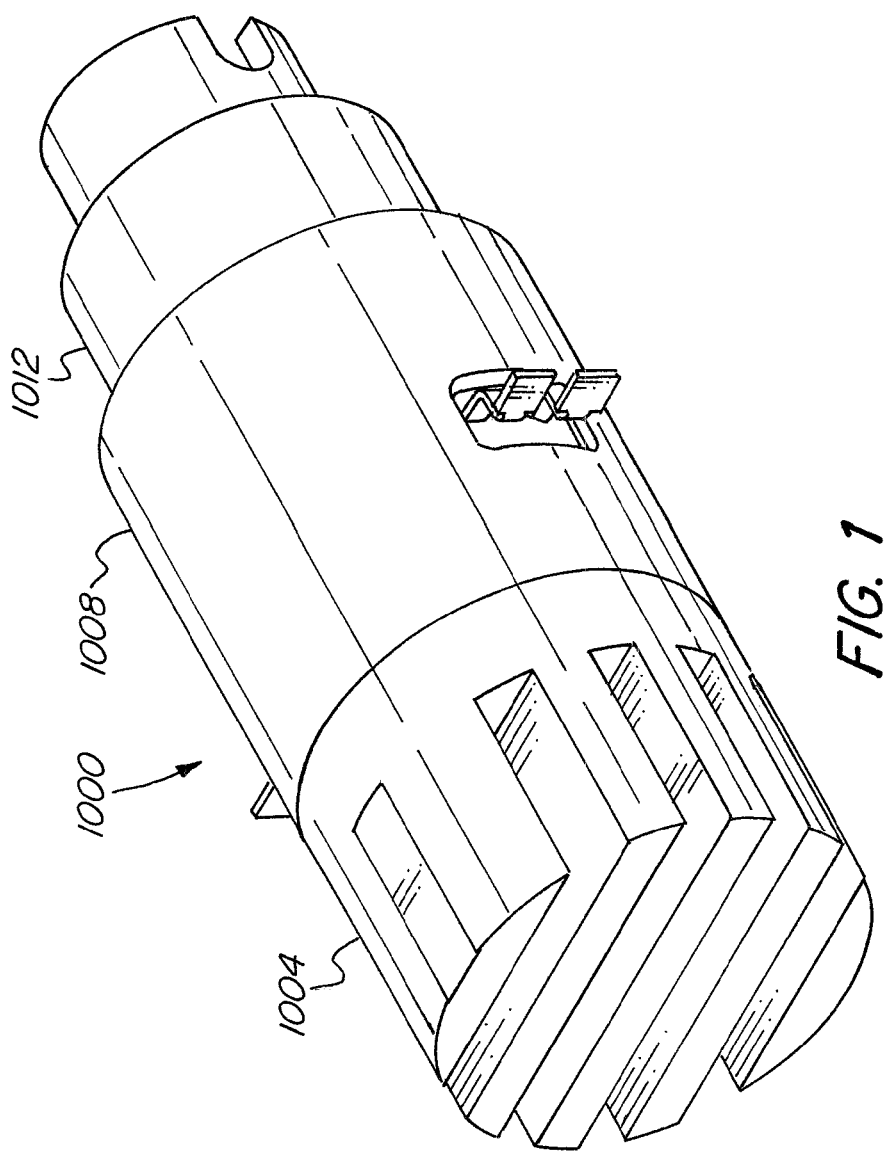
FIG. 1 is an isometric view of a light source according to the invention.

The basic components of one embodiment of a compact light source in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

Figure 2:
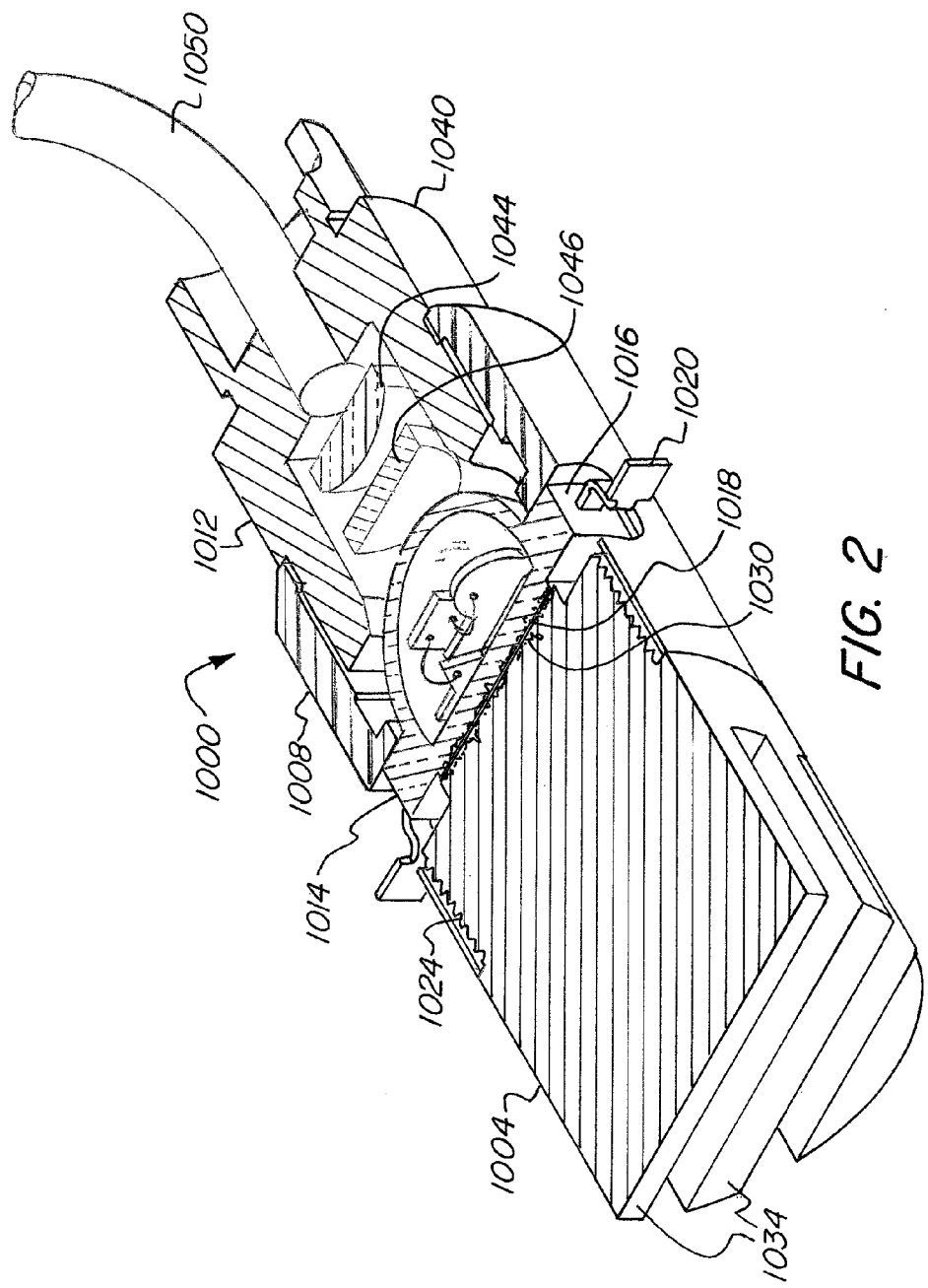
FIG. 2 is cross-sectional isometric view of a light source shown in FIG. 1.

FIGS. 1-2 illustrate one exemplary embodiment of a light source 1000 in accordance with the invention. Light source 1000 comprises a heat sink 1004, an insulation housing 1008, and a collimator 1012. A light emitting diode (LED) 1014 for generating light is disposed within insulation housing 1008. The LED 1014 includes a housing 1016 and surface 1018, and electrical leads 1020 control and power the LED 1014.

Figure 3:
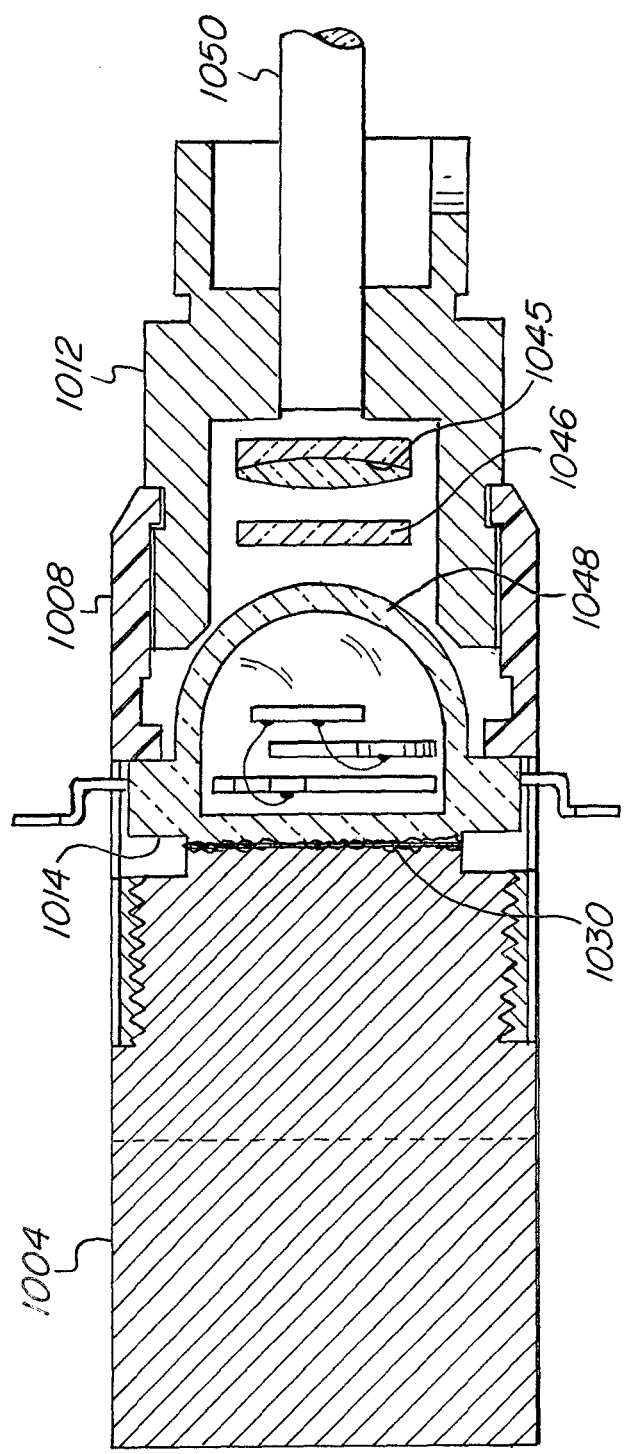
FIG. 3 is an cross-sectional view of a light source shown in FIG. 1.

As shown in FIGS. 2 and 3, both heat sink 1004 and housing 1008 are threaded, such that heat sink 1004 is coupled to housing 1008 via threads 1024. Heat sink 1004 can be screwed into housing 1008 until it abuts surface 1018 of LED 1014. It should also be noted that other, non-threaded coupling mechanisms may be employed for coupling the heat sink to 1004 to the housing 1008.

Surface 1018 is a generally flat surface made of a thermally conductive material, such as steel or aluminum, which provides a good interface for heat sink 1004. Surface 1018 is sufficiently conductive, and has sufficient surface area, to transfer significant heat from LED 1014 to heat sink 1004.

A thermal compound 1030 is sandwiched between surface 1018 and heat sink 1004. Thermal compound 1030 improves thermal conductance between LED 1014 and heat sink 1004. The medium of thermal compound is typically silicone grease. However, other appropriate substances may be used, such as mineral oil. The thermal compound may comprises any of various thermally conductive substances, including ceramic powders, such as beryllium oxide, aluminum nitride, aluminum oxide, zinc oxide, or silicon dioxide, metal conductors, such as silver or aluminum, carbon-based conductors, such as diamond powder or short carbon fibers, and liquid metals, such as gallium alloys. Alternatively, a phase change metal alloy can be used.

The thermal compound 1030, which has much better conductivity than air, improves the thermal conductivity of the interface between surface 1018 and heat sink 1004 by filling microscopic air gaps resulting from the imperfect nature of those surfaces. This use of a thermally conductive surface 1018 together with a thermal compound 1030 facilitates a very efficient transfer of heat generated by LED 1014 to heat sink 1004.

Meanwhile, insulation housing 1008 is made of a material of very low thermal conductance, thereby acting as an insulator to prevent the heat generated by LED 1014 from radiating outwardly from the light source 1000 in a radial direction. In advantageous embodiments, this insulation housing 1008 comprises polyimide. As a result, the area radially surrounding light source 1000, which may be a handheld device to which light source 1000 is mounted, as further explained below, is insulated from the heat produced by the LED 1014, which is instead channeled back into heat sink 1004 via surface 1018 and thermal compound 1030.

Heat sink 1004 comprises fins 1034 to improve the thermal conductance of heat sink 1004 with the ambient environment. Fins 1034 increase the surface area of the exterior of heat sink 1004, thereby increasing the contact area between the atmosphere and heat sink 1004. This improves the efficiency of heat sink 1004 by increasing the size of the interface between heat sink 1004 and the medium into which heat sink 1004 is dissipating the heat, thereby increasing the amount of heat that heat sink 1004 can channel from LED 1014 and emit into the environment. Heat sink 1004 may be made of a highly thermally conductive material, such as aluminum.

Collimator 1012, which is also coupled to housing 1008, includes an optics housing 1040 and collimating optics 1044. Collimator 1012 receives the light emitted from LED 1014 at one end, and at the other end, accommodates the distal end of a light guide 1050. The collimating optics 1044 narrow the light received from LED 1014 to focus it on the input of light guide 1050. This narrowing of the light may involve approximately collimating, or rendering parallel, the light rays, or reducing the cross-sectional area of the light beam, or both.

In order to accomplish this, the collimator 1012 may include one or more optical elements, including a positive lens for converging the light rays, such as plano-convex lens 1044 or a doublet 1045. This may be an aspheric lens 1044. Additionally, the LED housing 1016 itself may comprise an optical element 1048 for converging the light rays, such as a condenser lens. In addition, the interior of the collimator that accommodates collimating optics 1044 may have a reduced cross-section or an aperture stop to narrow the light beam. Additionally, a filter 1046, for filtering certain wavelengths of light, such as heat generating infrared light, may be disposed between LED 1014 and collimating optics 1044.

LED 1014 is powered and controlled via electrical leads 330. The brightness of LED 1014 can be controlled by varying the voltage supplied to leads 330. The brightness of LED 1014 can also be pulse-width modulated via leads 330, so that LED 1014 can be on for varying duty cycles, and the longer the duty cycle that LED 1014 is on, the more light it will output over time and the brighter LED 1014 will be.

Figure 4:
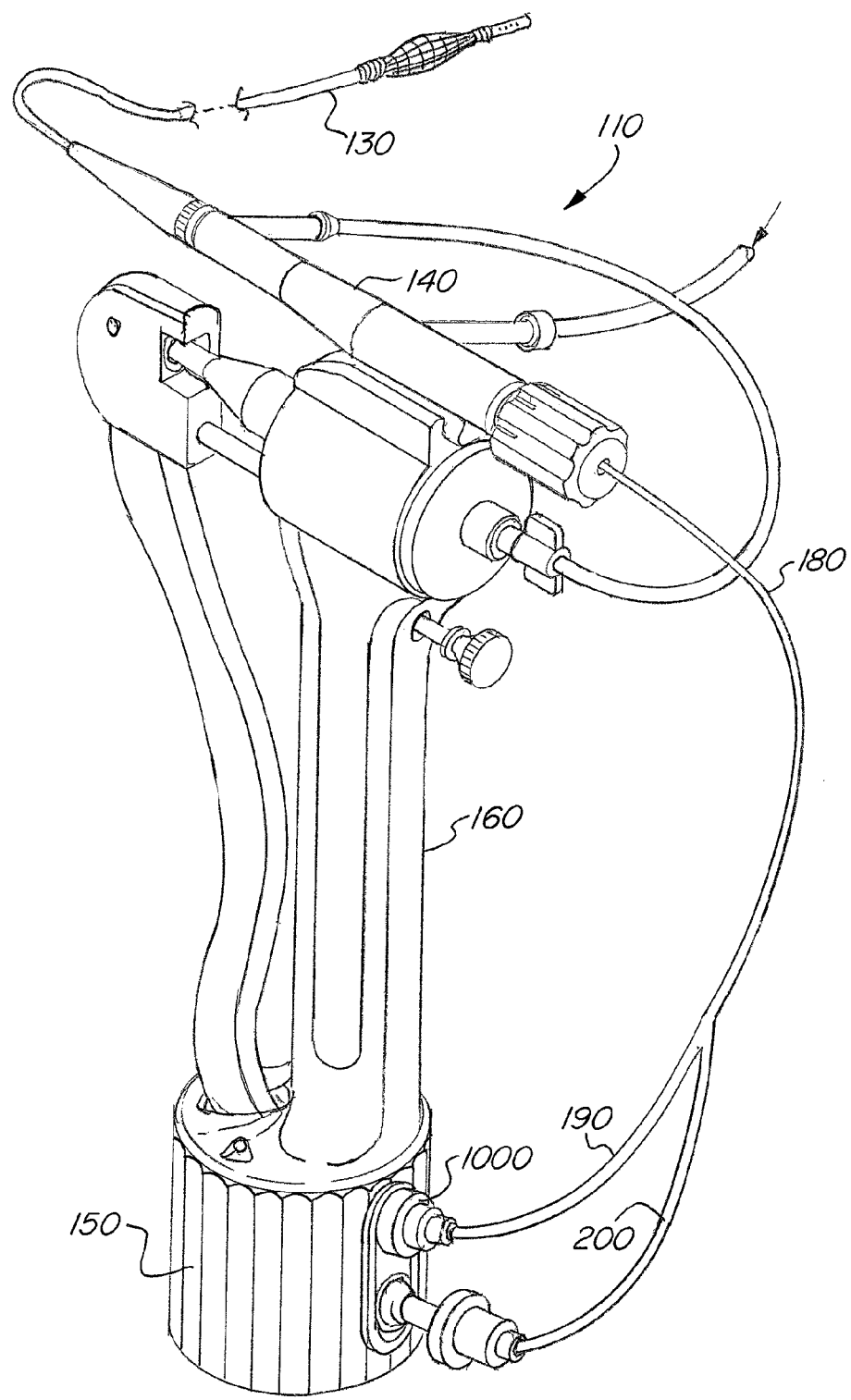
FIG. 4 is an isometric view of a catheter pump system incorporating the optics enclosure of FIG. 2 with a light source according to the embodiment shown in FIG. 1 mounted therein.

FIG. 4 is an isometric view of a handheld medical device 110 incorporating a light source 1000 in accordance with the present invention. Medical device 110 includes a handheld pump 160. A resector balloon catheter 130 and hub 140 are mounted to the top of the pump 160, and an imaging module 150 is coupled to the bottom of pump 160. An imaging device 180 is inserted into the rear of catheter hub 140, and is fed through a lumen of the hub 140 and catheter 130 and out through the distal tip of the catheter 130 in order to provide a surgeon with a view of the interior of a patient's body.

Figure 5:
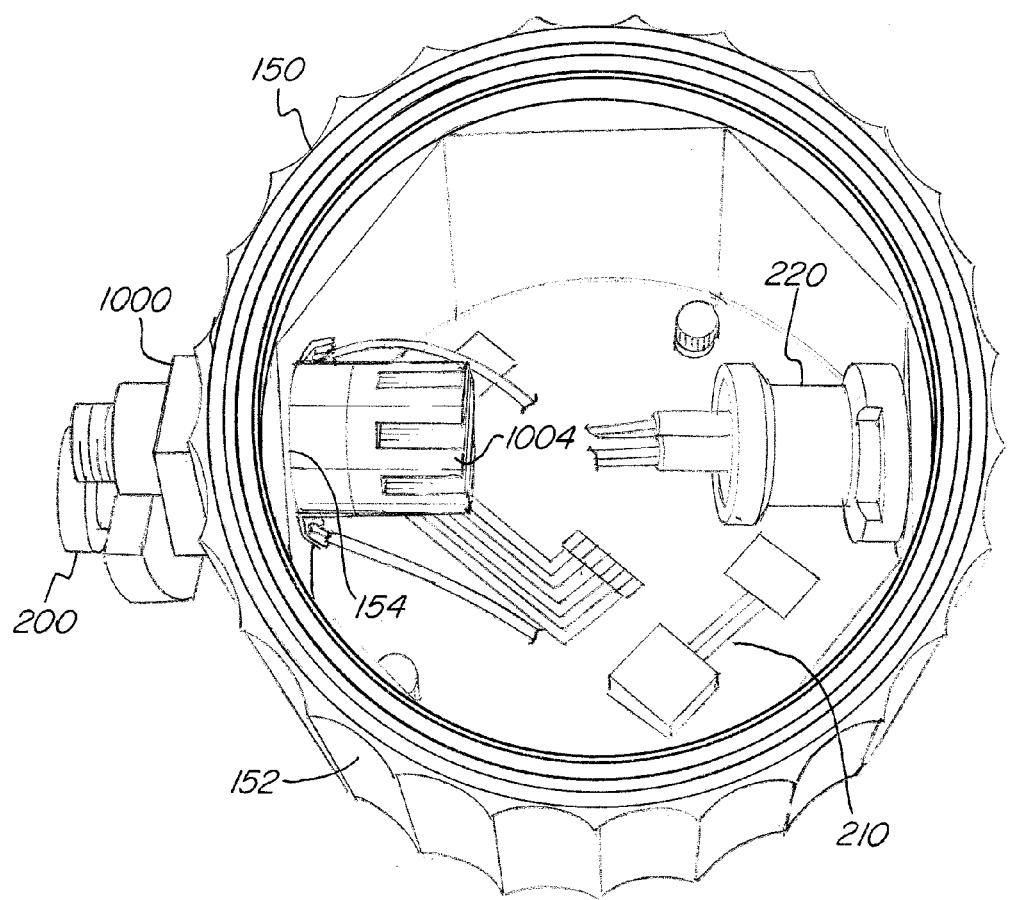
FIG. 5 is an isometric top view of an optics enclosure with the light source shown in FIG. 1 mounted therein.

The imaging device 180 incorporates a light guide 190 and image guide 200. Because the body interior must be illuminated in order to accomplish obtain images, light source 1000 provides light to imaging device 180 via light guide 190. This light travels through imaging device 180 and out the distal end thereof, where it reflects off the target site inside the patient's body. The reflected light travels back through the imaging device 180 to the imaging module 150 via image guide 200. Referring to FIG. 5, this optical signal is then processed by image circuitry 210 and output via USB port 220.

Imaging module 150 has a wall 152 with a hole 154 passing therethrough. Light source 1000 is mounted to wall 152 such that housing 1008 is partially disposed in the hole 154 and heat sink 1004 is disposed in the interior of imaging module 150. As a result, the insulation housing 1008 insulates the wall 152 from the heat generated by LED 1014, thereby preventing undesirable heating of the imaging module 150. This not only prevents injury to people using or touching the medical device 110, but it also prevents damage to other sensitive equipment in the device, such as the image guide 200 that is also mounted to the device.

Preventing inadvertent burns is not only important for avoiding injury to the medical practitioner using the device, but is extremely important for the patient, even if the patient is not directly in contact with the device, because it prevents shock and sudden uncontrolled reflexive movement of the practitioner, which would injure the patient during many types of delicate surgical procedures. Further, it prevents injury to patients who may be unconscious during a procedure and unable to move their bodies to avoid prolonged exposure to overheated parts.

Image guide 200 is optically coupled to image circuitry 210. Image circuitry 210 comprises a charge-coupled device (CCD) matrix, floating gate transistor matrix, or other means to convert images into digital or analog electrical information. Thus, image circuitry 210 produces an electrical representation of the optical signal (i.e. images) supplied by image guide 200, and comprises circuitry that facilitates the transfer of electrical image data to a computer.

For example, as shown in FIG. 5, image circuitry 210 includes a universal serial bus (USB) port 220 and necessary adaptation circuitry. In some embodiments, image circuitry 210 does little or no image processing to the data and merely converts the optical images to electrical data and transfers it to a computer. In those embodiments, the computer performs the image processing to produce a video feed or still images that are suitable for recording the procedure and/or providing the operator a live image feed of the site of the procedure within the patient's body.

It should be understood that the foregoing is illustrative and not limiting, and that obvious modifications may be made by those skilled in the art without departing from the spirit of the invention. Although the invention has been described with reference to embodiments herein, those embodiments do not limit the scope of the invention. Accordingly, reference should be made primarily to the accompanying claims, rather than the foregoing specification, to determine the scope of the invention.

What is claimed is:

1. A light source, comprising:
an LED for supplying light, said LED having a surface that conducts heat generated by said LED and having a portion that emits light;
an optical element that receives and transmits the light supplied by said LED;
a thermal insulation housing within which said LED is disposed for thermally insulating the LED such that said thermal insulation housing extends toward said optical element and beyond said portion of said LED that emits light;
a heat sink coupled to said thermal insulation housing and having a surface adjacent to the surface of said LED that conducts heat; and
a thermal compound disposed between the surface of said heat sink and the surface of said LED that conducts heat.

2. The light source of claim 1, wherein said insulation housing comprises polyimide.

3. The light source of claim 1, further comprising a collimator coupled to the insulation housing, wherein said optical element is disposed in said collimator.

4. The light source of claim 3, wherein said collimator comprises a receptacle adapted to receive a fiber optic cable.

5. The light source of claim 3, further comprising a light guide coupled to said collimator.

6. The light source of claim 3, wherein said optical element comprises a positive lens.

7. The light source of claim 3, wherein said optical element comprises an aspheric lens.

8. The light source of claim 3, wherein said optical element comprises a plano-convex lens.

9. The light source of claim 3, wherein said optical element comprises a doublet.

10. The light source of claim 1, further comprising a filter for filtering the light supplied by the LED.

11. The light source of claim 10, wherein said filter comprises an infrared filter.

12. The light source of claim 1, wherein said LED includes a condenser lens for transmitting the light.

13. The light source of claim 1, wherein said heat sink comprises an aluminum fin heat sink.

14. The light source of claim 1, wherein said thermal compound comprises a silicone medium.

15. The light source of claim 14, wherein said thermal compound is ceramic based.

16. The light source of claim 14, wherein said thermal compound is metal based.

17. The light source of claim 14, wherein said thermal compound is carbon based.

18. The light source of claim 1, wherein said surface of the LED that conducts heat comprises metal.

19. The light source of claim 1, wherein said LED is pulse-width modulated to control its light output.

20. The light source of claim 1, wherein said insulation housing and said heat sink are threaded such that said housing and heat sink screw together.

21. The light source of claim 1, further comprising an imaging module having a wall with a hole passing therethrough, wherein said insulation housing is at least partially disposed in the hole and mounted to said wall of said imaging module.

22. The light source of claim 1, wherein the LED includes a lens that transmits the light to said optical element.

* * * * *